United States Patent [19]

Kohnert et al.

[11] Patent Number: 5,352,452
[45] Date of Patent: Oct. 4, 1994

[54] STABILIZED COMPOSITIONS CONTAINING NON-GLYSYLATED HUMAN TISSUE TYPE PLASMINOGEN ACTIVATOR DERIVATIVE K2P PRO

[75] Inventors: Ulrich Kohnert, Habach; Rainer Rudolph, Weilheim, both of Fed. Rep. of Germany

[73] Assignee: Boehringer Mannheim GmbH, Mannheim-Waldhof, Fed. Rep. of Germany

[21] Appl. No.: 730,938
[22] PCT Filed: Dec. 19, 1990
[86] PCT No.: PCT/EP90/02250
§ 371 Date: Aug. 2, 1991
§ 102(e) Date: Aug. 2, 1991
[87] PCT Pub. No.: WO91/08765
PCT Pub. Date: Jun. 27, 1991

[30] Foreign Application Priority Data

Dec. 20, 1989 [DE] Fed. Rep. of Germany ....... 3942141

[51] Int. Cl.$^5$ ............ A61K 37/48; A61K 37/62; A61K 37/547; C12N 9/96
[52] U.S. Cl. ............ 424/94.64; 424/94.1; 424/94.3; 435/188
[58] Field of Search ............ 424/94.64, 94.1, 94.3; 435/188

[56] References Cited

U.S. PATENT DOCUMENTS

| | | | |
|---|---|---|---|
| 4,505,893 | 3/1985 | Mori et al. | 424/94.64 |
| 4,568,544 | 2/1986 | Hasegawa et al. | 424/94.1 |
| 4,837,022 | 6/1989 | Kakimoto et al. | 424/94.64 |
| 4,980,165 | 12/1990 | Isaacs et al. | 424/94.64 |
| 4,985,245 | 1/1991 | Kakimoto et al. | 424/94.64 |
| 5,068,106 | 11/1991 | Pâques et al. | 424/94.64 |
| 5,149,540 | 9/1992 | Kunihiro et al. | 424/94.3 |

FOREIGN PATENT DOCUMENTS

| | | |
|---|---|---|
| 0211592 | 2/1987 | European Pat. Off. |
| 0228862 | 7/1987 | European Pat. Off. |
| 0297294 | 1/1989 | European Pat. Off. |
| 3942142 | 6/1991 | Fed. Rep. of Germany |
| 3942143 | 6/1991 | Fed. Rep. of Germany |
| 3942144 | 6/1991 | Fed. Rep. of Germany |
| 3942145 | 6/1991 | Fed. Rep. of Germany |
| 9108765 | 6/1991 | PCT Int'l Appl. |

OTHER PUBLICATIONS

Larsen, G. R., et al., "Blood," vol. 73 (7), May 15, 1989, pp. 1842–1850.
Martin, V., et al., "Thrombosis Research," vol. 62 (3), pp. 137–146, 1991.
Kelley, R. F., et al., "Biochemistry," vol. 28, 1989, pp. 4047–4054.

Primary Examiner—Douglas W. Robinson
Assistant Examiner—Kristin K. Larson
Attorney, Agent, or Firm—Felfe & Lynch

[57] ABSTRACT

Stabilized compositions containing a non-glycosylated human tissue type plasminogen activator derivative are disclosed. The derivative is referred to as K2P pro. The composition has enzymatic activity of at least 1.1 mU/ml, a pH of from 4.5 to 6.5, and contains citrate as well as at least one of a variety of different compounds.

31 Claims, 1 Drawing Sheet

STABILIZED COMPOSITIONS CONTAINING NON-GLYSYLATED HUMAN TISSUE TYPE PLASMINOGEN ACTIVATOR DERIVATIVE K2P PRO

DESCRIPTION

Human tissue type plasminogen activator (t-PA) possesses a great therapeutic importance in the dissolution of blood coagula, for e.g. heart infarcts. t-PA brings about the dissolution of the blood coagula by the activation of plasminogen to plasmin. Plasmin in turn dissolves fibrin, the main component of the protein matrix of coagulated blood.

Natural t-PA is composed of several functional domains F, E, K1, K2 and P. The domain P contains the proteolytically-active centre which brings about the cleavage of plasminogen to plasmin. The gene technological production of t-PA or of different t-PA mutants, in which some of the domains F, E, K1 and K2 are deleted, in eukaryotic and prokaryotic cells is already known. In contrast to natural t-PA, these recombinant t-PA derivatives are synthesized in non-glycosylated form.

Furthermore, it is known that the sugar portion has considerable influence on the solubility and aggregation of proteins (J. Biol. Chem. 263 (1988), 8832–8837). It has now been ascertained that a non-glycosylated t-PA mutein with the domain composition K2P possesses substantially poorer solubility than glycosylated t-PA derivatives. The non-glycosylated t-PA variant dissolves to only a small extent in the buffers usually employed for the solubilization of proteins, such as e.g. 50 mmol/l. Na citrate, pH 6, 50 mmol/l. phosphate buffer or physiological NaCl solution. However, for the use as a therapeutically active material, the non-glycosylated t-PA derivative K2P pro should be present with a distinctly higher enzymatic activity of at least 1.4 MU/ml., preferably of 1.4 to 10 MU/ml.

From EP-A-0 217 379, it is known to increase the solubility of t-PA produced by prokaryotes (t-PA pro) by means of neutral or slightly alkaline arginine formulations. However, a disadvantage of this process is that good solubilities of t-PA pro can only be achieved with very high arginine concentrations. Furthermore, the stability of the highly concentrated t-PA derivative K2P pro is low under neutral or slightly alkaline conditions.

Consequently, it is the aim of the invention to develop formulations which contain the non-glycosylated t-PA derivative K2P pro with an enzymatic activity of at least 1.4 MU/ml., whereby the stability of the t-PA derivative is to remain over a comparatively long period of time.

The aim according to the invention is achieved by a pharmaceutical preparation of a non-glycosylated t-PA derivative K2P pro with an enzymatic activity of at least 1.4 MU/ml. and a pH value of 4.5 to 6.5, whereby this composition contains at least one compound from the group consisting of a) ascorbic acid,
b) EDTA,
c) a amino compound of the formula $$R^1R^2N-R-X$$

whereby $X=SO_3H$, $CH(NH_2)-CO_2H$, $CO_2H$, $H$, $NH_2$ or $OH$, $R=C_1-C_9$-alkylene, preferably $C_4-C_7$-alkylene, $C_3-C_6$-cycloalkylene or benzylidene and $R^1$ is H or $C_1-C_3$ alkyl and $R^2$ is H or $C_1-C_3$-alkyl, d) a guanidine analogue of the formula

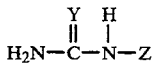

whereby $Y=H_2N^+$ or $O$, $Z=H$ or $(CH_2)_mV$, $(CH_2)_mCH(NH_2)-CO_2H$, $CH(CO_2H)-(CH_2)_mCO_2H$, wherein $V=NH_2$ or $CO_2H$ and $m=1$ to 4, e) a carboxylic acid substituted with one or more hydroxyl, keto and/or further carboxyl groups, f) dimethylbiguanide, g) a pyrimidine nucleoside are pyrimidine nucleotide and, h) trehalose, glucosemine, N-methylglucamine.

Figure 1:
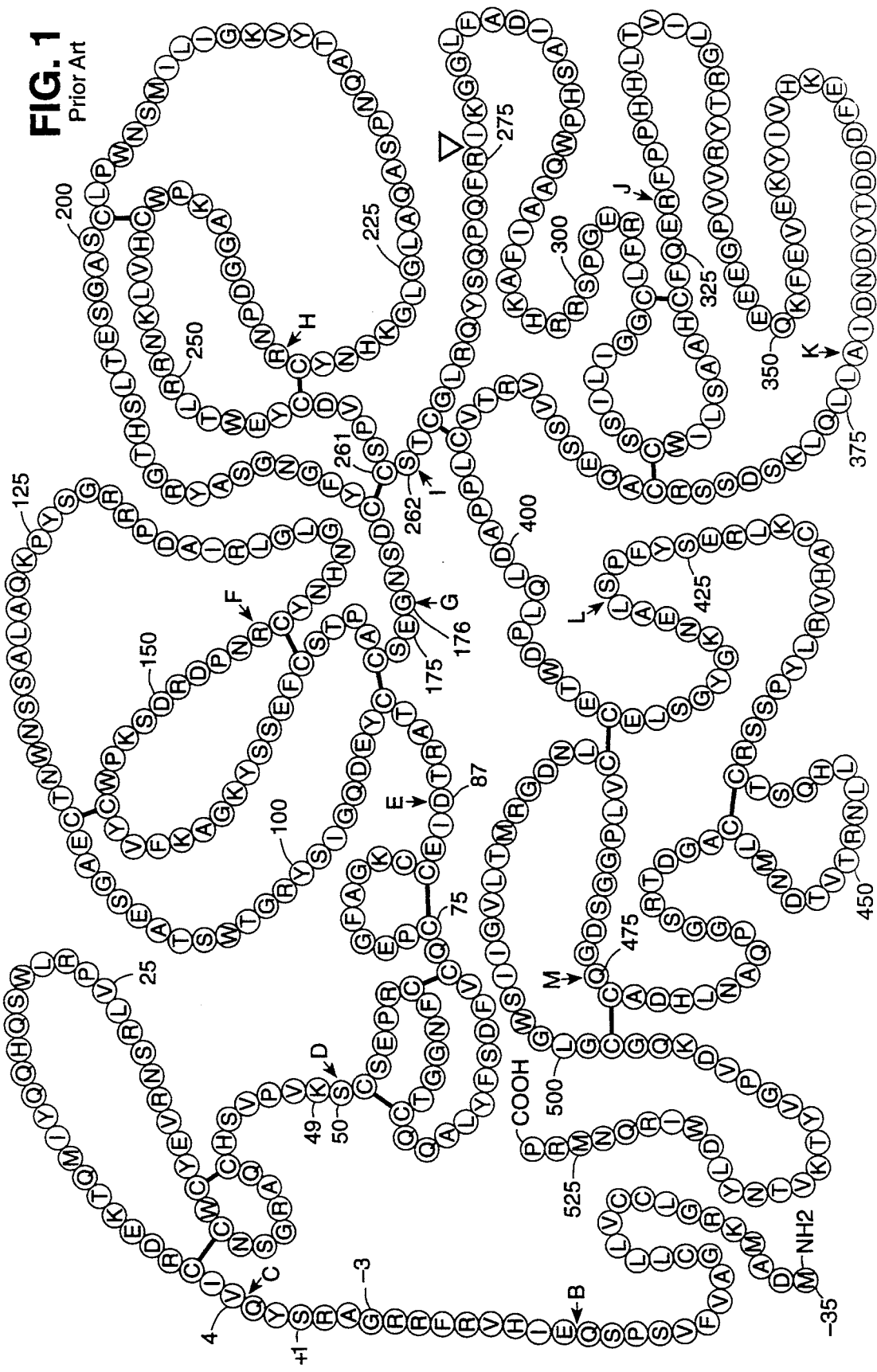
FIG. 1 Illustration of a t-PA molecule in the prior art.

By K2P pro according to the present invention, one understands a t-PA derivative which consists of the kringle 2- and of the protease domain and begins at any one of the amino acids 174–180 and ends with the amino acid 527. In addition, K2P pro can also contain part or all of the amino acids −3 (Gly) to +5 (Ile). A preferred protein is one which begins at amino acid 176 and, in front thereof, possibly also containing amino acids Ser, Tyr, Gln from the region −3 to +5. This designation follows the nomenclature given in T. J. R. Harris, Protein Engineering, Volume 1 (1987) 449–458 for t-PA. The production of such a t-PA derivative K2P pro is described in EP-A 0 382 174. The enzymatic activity for K2P pro is given as standard unit "U" according to the definition of the World Health Organization thereafter "WHO" for t-PA. The determination of the activity takes place according to H. Lill, ZGIMAL 42 (1987), 478–486.

For the solubilization of K2P pro, a citrate buffer has proved to be especially suitable. The citrate concentration is to amount e.g. to at least 5 mmol/l., preferably to 5 to 100 mmol/l., especially preferably to 50 mmol/l. The pH value is adjusted according to the alkalinity of the compound which is added, preferably with HCl or a base, such as e.g. NaOH or KOH.

Surprisingly, it was ascertained that the solubility of non-glycosylated K2P pro in a buffer other than a citrate buffer system, e.g. phosphate buffer, at equal ionic strength and equal pH value, is substantially smaller. It has proven to be suitable to adjust the pH value of alkaline citrate solutions with HCl, i.e., so that the composition also contains chloride ions. In the presence of chloride ions, surprisingly, highly concentrated solutions of non-glycosylated K2P pro are, substantially more stable than they are e.g. in the presence of phosphate ions. The pH value of acidic citrate solutions is usually adjusted with NaOH.

Suitable for a pharmaceutical composition according to the invention is a pH value between 4.5 and 6.5, a pH value of 5 to 6 being preferred. Surprisingly, in the case of the formulations usually employed for native t-PA with a pH value of >7, the stability of the non-glycosylated t-PA derivative K2P pro decreases considerably in such a solution. Thus, the single-chain form of K2P pro is only stable for a few days at room temperature or comparatively high temperatures at pH 7.2 and pH 8 in arginine-buffered solutions.

The pharmaceutical compositions according to the invention contain ascorbic acid, preferably of 0.1 to 1 mol/l., especially preferably of 0.2 to 0.3 mol/l.

The concentration of EDTA should preferably amount to 1 to 200 mol/l., especially preferably 10 to 100 mmol/l.

For a composition according to the invention, as amino compounds taurine, ε-aminocaproic acid, tranexamic acid, lysine, ornithine, δ-aminovaleric acid, p-aminomethylbenzoic acid, 8-aminooctanoic acid and/or 7-aminoheptanoic acid are preferred. Especially preferred is the use of ε-aminocaproic acid, p-aminomethylbenzoic acid, 7-aminoheptanoic acid, 8-aminooctanoic acid, tranexamic acid and/or lysine. The preferred concentrations amount to 0.5 to 20 mmol/l., and especially preferred to 1 to 10 mmol/l.

Also suitable are 4-aminobutanol-1, 5-aminopentanol-1, 6-aminohexanol-1, 1,9-diaminononane, 1,8-diaminooctane, 1,7-diaminoheptane, 1,6-diaminohexane, 1,5-diaminopentane, 1,4-diaminobutane and/or 1,3-diaminopropane. The concentrations of the α,ω-diamines and α,ω-aminoalcohols suitable for a preparation according to the invention preferably amount to 10 to 100 mmol/l.

Taurine and analogous compounds are preferably used with 0.1 to 0.5 mol/l., and especially preferred is a concentration of from 0.1 to 0.3 mol/l.

Furthermore, for a composition according to the invention, preferred guanidine-analogues compounds are urea, guanidinobutyric acid and/or arginine. The concentration of urea preferably amounts to 0.1 to 4 mol/l., with an especially preferred concentration of from 0.5 to 2 mol/l. For other guanidine-analogues compounds, the concentration preferably amounts to 10 to 200 mmol/l., 50 to 100 mmol/l being preferred.

As carboxylic acids which are substituted with hydroxyl, keto and/or further carboxyl groups malic acid, lactic acid, fumaric acid and/or 2-oxoglutaric acid are preferred examples. Their concentration preferably amounts to 0.001 to 1 mol/l. In an especially preferred embodiment, the concentration ranges from 0.01 to 0.5 mol/l.

Dimethylbiguanide is preferably used in concentrations of 50 to 400 mmol/l., especially of 100 to 300 mmol/l.

As pyrimidine nucleosides or pyrimidine nucleotides thymidine, cytosine and uridine or the corresponding nucleotides may be used. These substances are preferably used in concentrations of 1 to 300 mmol/l., especially of 10 to 300 mmol/l.

Trehalose, glucosamine and N-methylglucamine are preferably used in concentrations of 1 to 500 mmol/l., especially of 10 to 300 mmol/l.

Furthermore, a subject of the invention is a composition according to the invention which additionally contains one or more α-aminocarboxylic acids, especially histidine.

In the following is set out a series of especially preferred preparations according to the present invention. One formulation contains 50 mmol/l. Na citrate/HCl, pH 6, 2 mol/l. urea. A further formulation contains 50 mmol/l. Na citrate, pH 6, and 0.5 mol/l. to 1 mol/l. guanidine. Furthermore, a further formulation contains 50 mmol/l. Na citrate, pH 6, and 0.3 mol/l. taurine. Furthermore, an additional composition contains 50 mmol/l. Na citrate, pH 6, and 0.2 mol/l. to 0.3 mol/l. ascorbic acid. Yet another composition contains 50 mmol/l. Na citrate/HCl, pH 6, and 300 mmol/l. dimethylbiguanide. A further formulation contains 50 mmol/l. Na citrate/HCl, pH 6, and 10 to 300 mmol/l. thymidine, uridine or cytosine or 10 to 100 mmol/l. of one of the above-mentioned α,ω-diamines or one of the above-mentioned α,ω-aminoalcohols. Still another composition contains 50 mmol/l. Na citrate/HCl, pH 6, and 10 to 300 mmol/l. trehalose, glucosamine or N-methylglucamine.

Furthermore, an especially preferred composition according to the invention contains 50 mmol/l. Na citrate/HCl, pH 6, and 1 mmol/l. to 10 mmol/l. ε-aminocaproic acid, δ-aminovaleric acid, 7-aminoheptanoic acid, 8-aminooctanoic acid, p-aminomethylbenzoic acid, L-lysine, ornithine or tranexamic acid. Surprisingly, although in small molar excess (10 to 40 fold), these substances lead to outstanding solubility of K2P pro.

Further preferred are formulations which contain 50 mmol/l. Na citrate/HCl, pH 6, and a guanidine-analogue compound, especially arginine and guanidinobutyric acid, in a concentration of 50 to 100 mmol/l. A further formulation contains 50 mmol/l. Na citrate, pH 6, and 10 to 500 mmol/l. malic acid, lactic acid, fumaric acid or 2-oxoglutaric acid. Furthermore, a further formulation contains 50 mmol/l. Na citrate, pH 6, and 10 to 100 mmol/l. EDTA.

As is to be seen from the Examples, combinations of several of the above-mentioned compounds with citrate also bring about very good solubility of K2P pro. Suitable are e.g. combinations of lysine with arginine, ornithine, glucosamine and/or thymidine or of EDTA with ε-aminocaproic acid, lysine, arginine, glycosamine and/or thymidine. Also suitable are other combinations of at least two of the above-mentioned compounds with citrate.

Finally, a subject of the invention is also a medicament based on K2P pro as the active material in solution or as a lyophilisate with all the above-mentioned substances and possibly still further pharmaceutically compatible additive, adjuvant, carrier and filling materials.

The pharmaceutical preparations according to the invention are preferably used as injection and infusion solutions, i.e. a solution ready for injection is made available which possesses the composition according to the invention. However, it is also possible to make the pharmaceutical preparations in the form of lyophilisates. These are then reconstituted with known agents or solutions suitable for injection purposes. As injection medium, water which contains the usual additives used in injection solutions, such as stabilizing agents, solubilizing agents, buffers and isotonic additives, for example a physiological NaCl concentration, is preferred. Such additives are, for example, mannitol, tartrate or citrate buffers, ethanol, complex formers, such as e.g. ethylenediaminetetraacetic acid and its non-toxic salts, as well as high molecular weight polymers, such as liquid polyethylene oxide, for viscosity regulation. Liquid carrier materials for injection solutions must be sterile and are preferably filled into ampoules.

Finally, the present invention also comprises the use of K2P pro for the production of the pharmaceutical preparations according to the invention.

The following Examples explain further embodiments of the invention.

EXAMPLE 1

Influence of urea on the solubility of a non-glycosylated t-PA mutein with the domain composition K2P In this Example the influence of urea on the solubility of K2P pro (production according to EP-A 0 382 174) in citrate-buffered solutions at pH 6.0 is described. As is seen from Table 1, K2P pro is of only limited solubility in 50 mmol/l. citrate buffer at pH 6.0. By addition of urea, the solubility can be considerably improved. The optimum concentration of urea lies at about 2 mol/l. urea.

Protocol 170 ml. purified K2P pro (dissolved in 0.5 mol/l. arginine/$H_2PO_4$, pH 7.2) are concentrated by ultra-filtration over an AMICON YM 10 membrane. In each case, 1 ml. of the concentrate (activity 5.8 MU/ml.) is dialyzed against the buffers set out in Table 1. After centrifugation of the samples, the enzymatic activity is measured in the clear supernatant.

The enzymatic activity is given as volume activity in MU/ml. and as total activity in MU.

The measurement of the K2P activity can thereby be determined in the usual way by cleavage of a chromogenic substrate (H. Lill, ZGIMAL 42 (1987), 478–486). The unit U is a unit of the activity for t-PA according to the definition of the WHO, National Institute for Biological Standards and Control.

TABLE 1

| buffer | activity MU/ml. | MU |
| --- | --- | --- |
| 50 mmol/l. Na citrate/HCl, pH 6.0<br>8 mol/l. urea | 1.03 | 1.24 |
| 50 mmol/l. Na citrate/HCl, pH 6.0<br>6 mol/l. urea | 2.76 | 3.59 |
| 50 mmol/l. Na citrate/HCl, pH 6.0<br>4 mol/l. urea | 3.46 | 4.67 |
| 50 mmol/l. Na citrate/HCl, pH 6.0<br>2 mol/l. urea | 4.20 | 5.67 |
| 50 mmol/l. Na citrate/HCl, pH 6.0<br>1 mol/l. urea | 2.62 | 3.27 |
| 50 mmol/l. Na citrate/HCl, pH 6.0 | 0.32 | 0.93 |

EXAMPLE 2

Influence of various substances on the solubility of K2P pro

In this Example the influence of various substances on the solubility of K2P pro in citrate-buffered solutions at pH 6 is described. Outstanding solubilities (>2 MU/ml.) were achieved with taurine, dimethylbiguanide, glucosamine, trehalose, N-methylglucamine, uridine, cytidine, p-aminomethylbenzoic acid, fumaric acid and oxoglutaric acid. Furthermore, it is to be seen that the citrate buffer in the case of equal molar concentration, brings about a better solubility of the t-PA derivative than $NH_4HCO_3$, Tris or phosphate buffer.

Protocol:
see Example 1
Concentrate:
activity: 5.8 MU/ml.

TABLE 2

| buffer | activity MU/ml. | MU |
| --- | --- | --- |
| 50 mmol/l. Na citrate/HCl, pH 6.0<br>50 mmol/l. ornithine | 1.92 | 2.11 |
| 50 mmol/l. Na citrate/NaOH, pH 6.0<br>0.3 mol/l. taurine | 2.67 | 4.00 |
| 50 mmol/l. Na citrate/NaOH, pH 6.0<br>0.3 mol/l. ascorbic acid | 4.00 | 4.20 |
| 50 mmol/l. Na citrate/HCl, pH 6.0<br>10 mmol/l. EACA | 3.88 | 5.80 |
| 50 mmol/l. Na citrate/HCl, pH 6.0<br>10 mmol/l. L-lysine | 2.46 | 3.32 |
| 50 mmol/l. Na citrate/HCl, pH 6.0<br>10 mmol/l. tranexamic acid | 5.54 | 7.36 |
| 50 mmol/l. Na citrate/HCl, pH 6.0<br>0.3 mol/l. dimethylbiguanide | 2.96 | 3.40 |
| 50 mmol/l. Tris/HCl, pH 7.2 | 0.04 | 0.06 |
| 50 mmol/l. $NH_4HCO_3$ | 0.12 | 0.19 |
| 50 mmol/l. $Na_2HPO_4/H_3PO_4$, pH 7.2 | 0.15 | 0.23 |
| 50 mmol/l. Na citrate/HCl, pH 6.0 | 0.32 | 0.93 |
| 50 mmol/l. Na citrate/HCl, pH 6<br>0.3 mol/l. glucosamine | 2.02 | 2.02 |
| 50 mmol/l. Na citrate/HCl, pH 6<br>0.3 mol/l. trehalose | 3.52 | 3.17 |
| 50 mmol/l. Na citrate/HCl, pH 6<br>0.1 mol/l. thymidine | 1.57 | 1.88 |
| 50 mmol/l. Na citrate/HCl, pH 6<br>0.3 mol/l. uridine | 6.32 | 7.58 |
| 50 mmol/l. Na citrate/HCl, pH 6<br>30 mmol/l. cytosine | 3.8 | 4.94 |
| 50 mmol/l. Na citrate/HCl, pH 6<br>10 mmol/l. p-aminomethylbenzoic acid | 3.46 | 5.03 |
| 50 mmol/l. Na citrate/NaOH, pH 6<br>0.3 mol/l. malic acid | 1.53 | 1.68 |
| 50 mmol/l. Na citrate/NaOH, pH 6<br>0.3 mol/l. lactic acid | 1.59 | 1.98 |
| 50 mmol/l. Na citrate/NaOH, pH 6<br>0.3 mol/l. fumaric acid | 4.32 | 5.16 |
| 50 mmol/l. Na citrate/NaOH, pH 6<br>0.3 mol/l. 2-oxoglutaric acid | 4.24 | 4.66 |
| 50 mmol/l. Na citrate/HCl, pH 6<br>0.3 mol/l. N-methylglucamine | 3.36 | 3.70 |

EXAMPLE 3

Influence of ε-aminocaproic acid (EACA) on the solubility of K2P pro

Protocol:
see Example 1
Concentrate:
activity: 6.3 MU/ml.

TABLE 3

| buffer | activity MU/ml. | MU |
| --- | --- | --- |
| 50 mmol/l. Na citrate/HCl, pH 6.0 | 0.34 | 0.48 |
| 50 mmol/l. Na citrate/HCl, pH 6.0<br>10 mmol/l. EACA | 3.81 | 4.57 |
| 50 mmol/l. Na citrate/HCl, pH 6.0<br>5 mmol/l. EACA | 3.52 | 4.86 |
| 50 mmol/l. Na citrate/HCl, PH 6.0<br>1 mmol/l. EACA | 2.70 | 3.83 |
| 50 mmol/l. Na citrate/HCl, pH 6.0<br>0.1 mmol/l. EACA | 0.58 | 0.75 |

Table 3 shows chat EACA, even in a concentration of 1–10 mmol/l. (10–40 fold molar excess in comparison with K2P pro), brings about a considerable improvement of the solubility in citrate-buffered solutions at pH 6.0.

EXAMPLE 4

Influence of ascorbic acid on the solubility of K2P pro

Protocol:
see Example 1
Concentrate:

activity: 6.3 MU/ml.

TABLE 4

| buffer | activity MU/ml. | MU |
|---|---|---|
| 50 mmol/l. Na citrate/HCl, pH 6.0 | 0.34 | 0.48 |
| 50 mmol/l. Na citrate/NaOH, pH 6.0 0.3 mol/l. ascorbic acid | 4.04 | 4.24 |
| 50 mmol/l. Na citrate/NaOH, pH 6.0 0.2 mol/l. ascorbic acid | 2.40 | 2.93 |

The results of Table 4 show that, in citrate-buffered solution, the solubility of K2P pro is further increased by addition of ascorbic acid.

EXAMPLE 5 pH Dependency of the stability of K2P pro in arginine-containing solutions

Purified K2P pro is dialyzed against the 0.5 mol/l. Arg/$H_3PO_4$ buffer set out in Table 5 and stored in portions at −20°, 25° and 37° C. After 3, 7, 14 and 21 days, in each case, one sample is tested for activity and stimulatability by addition of fibrin and analyzed by SDS electrophoretically (starting values: activity: 1.3 MU/ml., stimulatability: 28). Stimulatability by addition to fibrin is synonymous with enhancement of catalytic efficiency of the enzyme in the presence of fibrin. See generally Harris et al., Protein Engineering, 1987 supra. The data summarized in Table 5 show that samples stored at pH 8 and pH 7.2 display, after 3 and 7 days storage, respectively, at 37° C., a distinct increase of the activity with simultaneous decrease of the stimulatability. At 25° C., it also results, however chronologically delayed, in an increase of the activity and decrease of the stimulatability. After 14 to 21 days, a reduction of the activity is then observed.

TABLE 5

| time | activity (MU/ml.)/stimulatability | | |
|---|---|---|---|
| | −20° C. | 25° C. | 37° C. |
| pH 8.0 | | | |
| 3 days | 1.22/36 | 1.47/24 | 1.45/15 |
| 7 days | 1.23/44 | 1.87/15 | 2.38/13 |
| 14 days | 1.37/33 | 2.08/9 | 1.1/10 |
| 21 days | 1.37/— | 2.14/10 | 1.0/7 |
| pH 7.2 | | | |
| 3 days | 1.12/39 | 1.5/27 | 1.7/20 |
| 7 days | 1.16/45 | 1.7/21 | 2.1/13 |
| 14 days | 1.38/32 | 1.7/9 | 1.9/9 |
| 21 days | 1.22/25 | 1.7/11 | 1.52/8 |
| pH 6.0 | | | |
| 3 days | 0.93/34 | 1.43/31 | 1.54/34 |
| 7 days | 1.05/46 | 1.27/42 | 1.58/36 |
| 14 days | 1.23/39 | 1.04/20 | 1.45/14 |
| 21 days | 1.43/26 | 0.95/16 | 1.00/8 |
| pH 5.5 | | | |
| 3 days | 0.85/32 | 1.47/40 | 1.08/39 |
| 7 days | 1.4/47 | 1.53/68 | 1.54/48 |
| 14 days | 1.2/32 | 1.3/26 | 1.3/24 |
| 21 days | 1.36/26 | 0.95/25 | 0.95/21 |

Parallel to these changes, a decrease of the molecular weight of K2P pro (electrophoresis with SDS-PAGE) is observed.

EXAMPLE 6

Influence of chloride and phosphate ions on the stability of K2P pro in arginine (Arg)-containing solutions Purified K2P pro is dialyzed against the arginine-containing buffers set out below and stored in portions at −20°, 25° and 37° C. After 2, 7 and 14 days, in each case 1 sample is analyzed by SDS-electrophoretically. It is shown that, in the presence of chloride ions, the single-chain form is substantially more stable than in the presence of phosphate ions. Whereas in chloride ion-containing solutions, after 7 days storage at 37° C. at pH 7.2 and 8, only 10% to 20% of the sample is cleaved, whereas in the phosphate-buffered solutions the proportion of the cleaved material amounts to 60% to 90%.

Buffers 0.5 mol/l. Arg/$H_3PO_4$, pH 8.0
0.5 mol/l. Arg/HCl, pH 8.0
0.5 mol/l. Arg/$H_3PO_4$, pH 7.2
0.5 mol/l. Arg/HCl, pH 7.2.

EXAMPLE 7

Influence of ε-aminocaproic acid on the solubility of K2P pro in citrate- and phosphate-buffered solutions Purified K2P pro is concentrated by ultra-filtration to 4.2 MU/ml. and dialyzed against the buffers given in Table 8 and centrifuged. After centrifuging of the samples, the activity is measured in the clear supernatant.

TABLE 6

| buffer | activity MU/ml. | MU |
|---|---|---|
| 50 mmol/l. Na citrate/HCl, pH 6.0 | 0.32 | 0.93 |
| 50 mmol/l. $Na_2HPO_4$/$H_3PO_4$, pH 6 | 0.07 | 0.10 |
| 50 mmol/l. Na citrate/HCl, pH 6 2 mmol/l. EACA | 3.30 | 4.60 |
| 50 mmol/l. $Na_2HPO_4$/$H_3PO_4$, pH 6 2 mmol/l. EACA | 0.90 | 1.39 |
| 50 mmol/l. Na citrate/HCl, pH 6 2 mmol/l. EACA 0.15 mol/l. NaCl | 2.43 | 3.52 |
| 50 mmol/l. $Na_2HPO_4$/$H_3PO_4$, pH 6 2 mmol/l. EACA 0.15 mol/l. NaCl | 1.08 | 1.57 |

Table 6 shows that the improvement of the solubility due to EACA in citrate-buffered solutions is considerably better than in phosphate buffers.

EXAMPLE 8

Influence of tranexamic acid (TEA) on the solubility of K2P pro see Example 1.
Concentrate:
activity: 4.2 MU/ml.

TABLE 7

| buffer | activity MU/ml. | MU |
|---|---|---|
| 50 mmol/l. Na citrate/HCl, pH 6.0 10 mmol/l. TEA | 2.66 | 3.60 |
| 50 mmol/l. Na citrate/HCl, pH 6 5 mmol/l. TEA | 2.54 | 3.30 |
| 50 mmol/l. Na citrate/HCl, pH 6 1 mmol/l. TEA | 2.35 | 3.29 |

The results show that with tranexamic acid (TEA)[1], a similar solubility of K2P pro is achieved as with EACA.

1) trans-4-aminomethylcyclohexanecarboxylic acid

EXAMPLE 9

Influence of ω-aminocarboxylic acids on the solubility of K2P pro (The results of this experiment set forth in example 9 follow in Table 8.)

Protocol:

see Example 1
Concentrate:
activity: 4.2 MU/ml.

TABLE 8

| buffer | activity | |
|---|---|---|
| | MU/ml. | MU |
| 50 mmol/l. Na citrate/HCl, pH 6 | 0.32 | 0.93 |
| 50 mmol/l. Na citrate/HCl, pH 6<br>10 mmol/l. 8-aminooctanoic acid | 3.12 | 4.05 |
| 50 mmol/l. Na citrate/HCl, pH 6<br>10 mmol/l. 7-aminoheptanoic acid | 3.54 | 4.42 |
| 50 mmol/l. Na citrate/HCl, pH 6<br>10 mmol/l. EACA | 4.22 | 2.90 |
| 50 mmol/l. Na citrate/HCl, pH 6<br>10 mmol/l. δ-aminovaleric acid | 1.83 | 2.47 |

EXAMPLE 10

Influence of guanidine analogues on the solubility of K2P pro

Protocol:
see Example 1
Concentrate:
activity: 4.2 MU/ml.

TABLE 9

| buffer | activity | |
|---|---|---|
| | MU/ml. | MU |
| 50 mmol/l. Na citrate/HCl, pH 6<br>50 mmol/l. arginine | 1.42 | 2.06 |
| 50 mmol/l. Na citrate/HCl, pH 6<br>50 mmol/l. guanidinobutyric acid | 2.21 | 3.08 |

The results show that the solubility of K2Ppro is clearly improved with a guanidino group.

EXAMPLE 11

Influence of EDTA on the solubility behaviour of K2P pro

Protocol:
see Example 1
Concentrate:
activity: 4.2 MU/ml.

TABLE 10

| buffer | activity | |
|---|---|---|
| | MU/ml. | MU |
| 10 mmol/l. EDTA/NaOH, pH 6 | 0.02 | 0.03 |
| 0.3 mol/l. EDTA/NaOH, pH 6 | 1.95 | 1.95 |
| 50 mmol/l. Na citrate/NaOH, pH 6<br>50 mmol/l. EDTA | 1.80 | 2.25 |
| 50 mmol/l. Na citrate/NaOH, pH 6<br>100 mmol/l. EDTA | 3.36 | 4.03 |
| 50 mmol/l. Na citrate/HCl, pH 6 | 0.32 | 0.93 |

Table 10 shows that the combination of EDTA with citrate has more than an additive effect on the solubility of K2P pro.

EXAMPLE 12

Influence of amino acids alone or in combination on the solubility of K2P Pro (The results of this experiment set forth in example 12 follow in Table 11.)

Protocol:
see Example 1
Concentrate:
activity: 4.2 MU/ml.

TABLE 11

| buffer | activity | |
|---|---|---|
| | MU/ml. | MU |
| 50 mmol/l. Na citrate/HCl, pH 6<br>50 mmol/l. arginine | 1.42 | 2.06 |
| 50 mmol/l. Na citrate/HCl, pH 6<br>10 mmol/l. L-lysine | 2.81 | 3.94 |
| 50 mmol/l. Na citrate/HCl, pH 6<br>1 mmol/l. L-lysine | 2.00 | 2.6 |
| 50 mmol/l. Na citrate/HCl, pH 6<br>10 mmol/l. L-lysine<br>10 mmol/l. arginine | 2.56 | 3.84 |
| 50 mmol/l. Na citrate/HCl, pH 6<br>10 mmol/l. lysine<br>50 mmol/l. arginine | 3.27 | 4.9 |
| 50 mmol/l. Na citrate/HCl, pH 6<br>10 mmol/l. lysine<br>10 mmol/l. arginine<br>10 mmol/l. ornithine | 3.18 | 4.13 |
| 50 mmol/l. Na citrate/HCl, pH 6<br>10 mmol/l. lysine<br>50 mmol/l. arginine<br>10 mmol/l. ornithine | 2.70 | 3.78 |
| 50 mmol/l. Na citrate/HCl, pH 6<br>10 mmol/l. lysine<br>50 mmol/l. arginine<br>50 mmol/l. ornithine | 3.34 | 4.30 |

EXAMPLE 13

Influence of ω-aminoalcohols on the solubility of K2P pro (The results of this experiment set forth in example 13 follow in Table 12.)

Protocol:
see Example 1
Concentrate:
activity: 4.9 MU/ml.

TABLE 12

| buffer | activity | |
|---|---|---|
| | MU/ml. | MU |
| 50 mmol/l. Na citrate/HCl, pH 6<br>50 mmol/l. 4-aminobutanol-1 | 1.84 | 2.4 |
| 50 mmol/l. Na citrate/HCl, pH 6<br>50 mmol/l. 5-aminopentanol-1 | 2.54 | 3.55 |

EXAMPLE 14

Influence of various substances in combination of the solubility of K2P pro (The results of this experiment set forth in example 14 follow in Table 13.)

Protocol:
see Example 1
Concentrate:
activity: 5.5 MU/ml.

TABLE 13

| buffer | activity | |
|---|---|---|
| | MU/ml. | MU |
| 50 mmol/l. Na citrate, pH 6<br>50 mmol/l. EDTA<br>1 mmol/l. EACA<br>50 mmol/l. glucosamine | 4.24 | 5.08 pH |
| 50 mmol/l. Na citrate, pH 6<br>10 mmol/l. EDTA<br>1 mmol/l. EACA<br>10 mmol/l. glucosamine | 3.63 | 5.08 |
| 50 mmol/l. Na citrate, pH 6<br>10 mmol/l. EDTA<br>1 mmol/l. EACA<br>10 mmol/l. glucosamine<br>50 mmol/l. thymidine | 3.70 | 5.14 |
| 50 mmol/l. Na citrate, pH 6 | 4.00 | 5.40 |

TABLE 13-continued

| buffer | activity MU/ml | MU |
|---|---|---|
| 50 mmol/l. EDTA<br>1 mmol/l. lysine<br>50 mmol/l. glucosamine | | |
| 50 mmol/l. Na citrate, pH 6<br>50 mmol/l. EDTA<br>1 mmol/l. lysine<br>10 mmol/l. glucosamine | 3.04 | 3.95 |
| 50 mmol/l. Na citrate, pH 6<br>10 mmol/l. EDTA<br>1 mmol/l. lysine<br>10 mmol/l. glucosamine<br>10 mmol/l. thymidine | 3.12 | 4.52 |
| 50 mmol/l. Na citrate, pH 6<br>10 mmol/l. EDTA<br>1 mmol/l. lysine<br>10 mmol/l. arginine<br>10 mmol/l. glucosamine<br>10 mmol/l. thymidine | 2.60 | 3.77 |
| 50 mmol/l. Na citrate, pH 6<br>10 mmol/l. EDTA<br>1 mmol/l. lysine<br>25 mmol/l. arginine<br>10 mmol/l. glucosamine<br>10 mmol/l. thymidine | 2.94 | 4.12 |
| 50 mmol/l. Na citrate, pH 6<br>1 mmol/l. lysine<br>10 mmol/l. arginine<br>10 mmol/l. glucosamine<br>10 mmol/l. thymidine | 2.80 | 3.64 |
| 50 mmol/l. Na citrate, pH 6<br>10 mmol/l. EDTA<br>1 mmol/l. lysine<br>25 mmol/l. arginine<br>10 mmol/l. glucosamine<br>25 mmol/l. thymidine | 3.20 | 4.32 |
| 50 mmol/l. Na citrate, pH 6<br>10 mmol/l. EDTA<br>1 mmol/l. lysine<br>25 mmol/l. arginine<br>10 mmol/l. glucosamine<br>50 mmol/l. thymidine | 4.56 | 5.90 |
| 50 mmol/l. Na citrate, pH 6<br>1 mmol/l. lysine<br>25 mmol/l. arginine<br>10 mmol/l. glucosamine<br>50 mmol/l. thymidine | 3.24 | 4.54 |
| 50 mmol/l. Na citrate, pH 6<br>1 mmol/l. lysine<br>25 mmol/l. arginine<br>10 mmol/l. glucosamine<br>25 mmol/l. thymidine | 3.54 | 4.95 |
| 40 mmol/l. Na citrate, pH 6<br>1 mmol/l. lysine<br>25 mmol/l. arginine<br>50 nmol/l. glucosamine<br>25 mmol/l. thymidine | 3.60 | 4.68 |
| 50 mmol/l. Na citrate, pH 6<br>1 mmol/l. lysine<br>25 mmol/l. arginine<br>100 mmol/l. glucosamine<br>25 mmol/l. thymidine | 5.85 | 5.85 |

EXAMPLE 15

Influence of α,ω-diamine on the solubility of K2P pro
(The results of this experiment set forth in example 15 follow in Table 14.)

Protocol:
see Example 1
Concentrate:
activity: 4.9 MU/ml.

TABLE 14

| buffer | activity MU/ml. | MU |
|---|---|---|
| 50 mmol/l. Na citrate/HCl, pH 6<br>50 mmol/l. 1,9-diaminononane | 3.12 | 4.05 |
| 50 mmol/l. Na citrate/HCl, pH 6<br>50 mmol/l. 1,8-diaminooctane | 2.80 | 3.64 |
| 50 mmol/l. Na citrate/HCl, pH 6<br>50 mmol/l. 1,6-diaminohexane | 3.42 | 4.45 |
| 50 mmol/l. Na citrate/HCl, pH 6<br>50 mmol/l. 1,5-diaminopentane | 3.52 | 4.40 |
| 50 mmol/l. Na citrate/HCl, pH 6<br>50 mmol/l. 1,4-diaminobutane | 3.96 | 5.15 |
| 50 mmol/l. Na citrate/HCl, pH 6<br>50 mmol/l. 1,3-diaminopropane | 3.33 | 4.23 |

We claim:

1. A stabilized composition having human tissue type plasminogen activator (t-PA) activity consisting essentially of non-glycosylated t-PA derivative K2P Pro having enzymatic activity of at least 1.4 MU/ml, citrate, and at least one compound selected from the group consisting of:

(a) ascorbic acid;
(b) EDTA;
(c) an amino compound of the formula $$R^1R^2N-R-X$$

wherein:
x is $SO_3H$, $CH(NH_2)-CO_2H$, $CO_2H$, H, $NH_2$ or OH;
R is a $C_1-C_9$ alkylene, $C_3-C_6$ cycloalkylene or benzylidene and
$R^1$ is H or $C_1-C_3$ alkyl and $R^2$ is H or $C_1-C_3$ alkyl;

(d) a guanidine analogue of formula $$H_2N-\overset{\overset{Y}{\|}}{C}-NH-Z$$

whereby
Y is $NH_2$ or O;
Z is H, $(CH_2)_m CH(NH_2)-CO_2H$, $CH(CO_2H)-(CH_2)_m$, $CO_2H$, or $(CH_2)_m V$, where V is $NH_2$, or COOH and m is a number from 1 to 4;

(e) a carboxylic acid substituted at least once with a hydroxyl group, keto group, or a carboxyl group;
(f) dimethylbiguanide;
(g) a pyrimidine nucleoside;
(h) a pyrimidine nucleotide;
(i) trehalose;
(j) glucosamine; and
(k) N-methylglucamine, said composition having a pH of from 4.5 to 6.5.

2. The stabilized composition of claim 1, wherein said amino compound is selected from the group consisting of taurine, Σ-amino caproic acid, tranexamic acid, lysine, ornithine, δ-aminovaleric acid, p-amino methylbenzoic acid, 4-amino butanol-1, 5-amino pentanol-1, 6-aminohexanol-1, 1,9-diaminononane, 1,8-diaminooctane, 1,7-diaminoheptane, 1,6-diaminohexane, 1,5-diamino pentane, 1,4-diaminobutane, 1,3-diaminopropane, 8-aminooctanoic acid, and 7-amino heptanoic acid.

3. The stabilized composition of claim 1, wherein said guanidine analogue is urea, guanidinobutyric acid or arginine.

4. The stabilized composition of claim 1, wherein said carboxylic acid is malic acid, lactic acid, fumaric acid or 2-oxoglutaric acid.

5. The stabilized composition of claim 1, wherein said citrate is present at a concentration of from 5 to 100 mmol/l.

6. The stabilized composition of claim 5, wherein said citrate is present at a concentration of 50 mmol/l.

7. The stabilized composition of claim 1, further comprising a chloride ion.

8. The stabilized composition of claim 1, having 50 mmol/l of sodium citrate, from 0.1 to 1 mol/l ascorbic acid, and a pH of 6.0.

9. The stabilized composition of claim 8, comprising ascorbic acid at a concentration of from 0.2 to 0.3 mol/l.

10. The stabilized composition of claim 1, having 50 mmol/l sodium citrate, from 1 to 200 mmol/l EDTA, and a pH of 6.

11. The stabilized composition of claim 10, comprising from 10 to 100 mmol/l EDTA.

12. The stabilized composition of claim 1, having 50 mmol/l sodium citrate, from 0.1 to 0.5 mol/l taurine, and a pH of 6.

13. The stabilized composition of claim 12, comprising from 0.1 to 0.3 mol/l taurine.

14. The stabilized composition of claim 1, having 50 mmol/l sodium citrate, and from 0.5 to 20 mmol/l of a compound selected from the group consisting of ε-aminocaproic acid, δ-amino-valeric acid, lysine, ornithine, tranexamic acid, p-aminoethyl benzoic acid, 7-aminoheptanoic acid and 8-aminooctanoic acid and a pH of 6.

15. The stabilized composition of claim 14, wherein said compound is present at a concentration of from 1 to 10 mmol/l.

16. The stabilized composition of claim 1, having 50 mmol/l sodium citrate/HCl, and from 10 to 100 mmol/l of a compound selected from the group consisting of 4-aminobutanol-1; 5-aminopentanol-1; 6-aminohexanol-1; 1,9-diaminononane; 1,8-diaminooctane; 1,7-diaminoheptane; 1,6-diaminohexane, 1,5-diaminopentane; 1,4-diaminobutane and 1,3-diaminopropane, said composition having a pH of 6.

17. The stabilized composition of claim 1, having 50 mmol/l sodium citrate/HCl and from 0.1 to 4 mol/l urea, said composition having a pH of 6.

18. The stabilized composition of claim 17, comprising urea at a concentration of 0.5 to 2 mol/l.

19. The stabilized composition of claim 1, having 50 mmol/l sodium citrate/HCl and from 10 to 200 mmol/l of a compound selected from the group consisting of guanidinobutyric acid and arginine, said composition having a pH of 6.

20. The stabilized composition of claim 19, wherein said compound is present at a concentration of from 50 to 100 mmol/l.

21. The stabilized composition of claim 1, having 50 mmol/l sodium citrate, and from 0.001 to 1 mol/l of a compound selected from the group consisting of malic acid, lactic acid, fumaric acid and 2-oxoglutaric acid, said composition having a pH of 6.

22. The stabilized composition of claim 21, wherein said compound is present at a concentration of from 0.01 to 5 mol/l.

23. The stabilized composition of claim 1, having 50 mmol/l sodium citrate/HCl, and from 50 to 400 mmol/l dimethylbiguanide, said composition having a pH of 6.

24. The stabilized composition of claim 23, comprising dimethylbiguanide at a concentration of from 100 to 300 mmol/l.

25. The stabilized composition of claim 1, having 50 mmol/l sodium citrate/HCl, and from 1 to 300 mmol/l of a compound selected from the group consisting of thymidine, cytosine, and uridine, said composition having a pH of 6.

26. The stabilized composition of claim 25, wherein said compound is present in a concentration of from 10 to 300 mmol/l.

27. The stabilized composition of claim 1, having 50 mmol/l sodium citrate/HCl, and from 1 to 500 mmol/l of a compound selected from the group consisting of trehalose, glucosamine and N-methylglucamine, said composition having a pH of 6.

28. The stabilized composition of claim 27, wherein said compound is present at a concentration of from 10 to 300 mmol/l.

29. The stabilized composition of claim 1, having 50 mmol/l sodium citrate and a pH of 6.

30. The stabilized composition of claim 1, further comprising a pharmaceutically acceptable carrier.

31. The stabilized composition of claim 1 wherein R is $C_4$–$C_7$ alkylene.

* * * * *